United States Patent [19]
Bauerfeind et al.

[11] Patent Number: 5,395,306
[45] Date of Patent: Mar. 7, 1995

[54] ONE-PART BANDAGE FOR THE CLAVICLE

[75] Inventors: Hans B. Bauerfeind, Kempen; Rainer Scheuermann, Kiel, both of Germany

[73] Assignee: Bauerfeind & Co., Germany

[21] Appl. No.: 39,962

[22] Filed: Mar. 30, 1993

[30] Foreign Application Priority Data

Apr. 2, 1992 [DE] Germany .......... 42 11 023.8

[51] Int. Cl.[6] ............................................. A61F 5/00
[52] U.S. Cl. ................................. 602/61; 602/19; 128/876; 128/DIG. 15; 128/DIG. 19; 606/203
[58] Field of Search ................... 602/5, 19, 41, 75–78, 602/4, 20, 53, 60–62; 2/44, 45, 92; 128/869–876, DIG. 15, DIG. 19; 606/203; 224/150, 267, 901

[56] References Cited

U.S. PATENT DOCUMENTS

| 945,359 | 1/1910 | Adams | 602/19 |
|---|---|---|---|
| 2,723,664 | 11/1955 | Davis | 602/19 |
| 3,191,599 | 6/1965 | Kendell | 128/875 |
| 4,479,267 | 10/1984 | Radowsky, Jr. | 2/44 X |
| 4,901,713 | 2/1990 | Troeger | 602/4 |
| 5,015,251 | 5/1991 | Cherubini | 606/203 |
| 5,105,828 | 4/1992 | Grant | 128/876 |

FOREIGN PATENT DOCUMENTS

| 3901918 | 7/1990 | Germany | 602/19 |
|---|---|---|---|
| 2159058 | 11/1985 | United Kingdom | 602/19 |

*Primary Examiner*—Richard J. Apley
*Assistant Examiner*—Linda C. M. Dvorak

[57] ABSTRACT

A one-part bandage for the clavicle, with a back strap extending crosswise over the back, to which shoulder straps are connected which cross under the armpits and extend over a clavicle. The straps cross in the region of the middle of the back strap at the crossing place, and run out over the hips to the abdomen into connecting end parts, whereby the end parts are joined together by means of an adhesive seal. This configuration is made of non-elastic strap material. The shoulder straps are applied at places that are distanced from one another on the back strap on its side turned away from the back, whereby support places are each formed by an adhesive seal, whose adhesive part is introduced on the back strap and whose coating part completely covering the respective adhesive part is formed by the respective shoulder strap.

4 Claims, 1 Drawing Sheet

ONE-PART BANDAGE FOR THE CLAVICLE

BACKGROUND OF THE INVENTION

The invention concerns a one part bandage for the clavicle. The bandage has a back strap extending crosswise over the back to which shoulder straps are connected which run under the armpits and extend over the clavicle. The shoulder straps cross in the region of the center of the back strap at a crossing place and extend into connecting end parts over the hips and over the abdomen. The end parts are joined together by means of an adhesive seal formed of synthetic materials which adhere when pressed together, for example a Velcro strip which has a multiplicity of hooks that adhere to a soft matted fabric that serves as loops.

DESCRIPTION OF THE PRIOR ART

A bandage as a support board is known from DE GM 1,932,745, i.e., as a means for improving posture. For this purpose, the bandage consists of an elastic band, whose shoulder straps cross loosely over the center of the back strap. Due to the compliance of the band, if the back of the person who wears this bandage is bent, this band exercises an increasing pressure on the person with increasing bending of the back and thus to a certain extent reminds the person of the fact that an undesired position is being assumed with respect to a healthy posture. Such a bandage is also called a "warning bandage". Thus it is also obviously desired to allow a possible shifting of the crossing position of the shoulder straps in the region of the back strap, since the shoulder straps are only loosely lying over the back strap.

SUMMARY OF THE INVENTION

The invention provides a one-part bandage, which provides a specific therapeutic treatment by applying pressure onto the clavicle, e.g., in the case of spraining a shoulder joint or of a clavicle fracture. For this purpose, the bandage is made of nonelastic strap material with shoulder straps that lie at positions that are distanced from one another on the back strap on the side turned away from the back. The support positions are formed by adhesive seals, the Velcro strips. The adhesive part is disposed to the back strap and the coating part completely covers the respective adhesive part that is formed by the respective shoulder strap.

Because of the configuration of the bandage, a uniform tension of the bandage can be produced and the bandage adapts to the body volume of the patient so that the necessary length of the back strap and shoulder straps is automatically adjusted because the shoulder strap (as the coating part) is disposed over the adhesive part and is simply pressed onto the latter, whereby the relative position of the adhesive seal thus formed is produced by itself with respect to the concerned shoulder strap with a more or less tight application of the bandage. Due to the complete covering of the respective adhesive part by the shoulder strap belonging to it, the adhesive part cannot produce undesired scratching effects with respect to the patient's clothing, effects which could possibly damage the clothing. By sealing the bandage by pressing the adhesive seal of the end parts, a satisfactory application of the entire bandage onto the body of the patient results, whereby the tension exercised on the clavicle remains uniform, since the bandage is secured primarily in the region of the shoulder straps and the back strap by the respective adhesive seals. The adhesive seal also assures this securing since the adhesive seal in turn can take up tensile stresses acting on the bandage.

The bandage can appropriately be formed throughout as a coating part, that is the loops, which covers the adhesive part, that is the hooks of the adhesive seal. In this case, with respect to the shoulder straps, there is a possibility for unlimited adaptation of the length of the shoulder straps with respect to the adhesive seals introduced onto the back strap.

A favorable position of the shoulder straps is produced particularly if the adhesive seals on the back strap maintain a distance such that the crossing place of the shoulder straps lies above the back strap, not overlapping the latter. In this case, there results a close clinging of the shoulder straps in the region of the armpits and the clavicle and thus a particularly uniform tension of the bandage with respect to the clavicle which is being treated.

DESCRIPTION OF THE PREFERRED EMBODIMENTS

Figure 2:
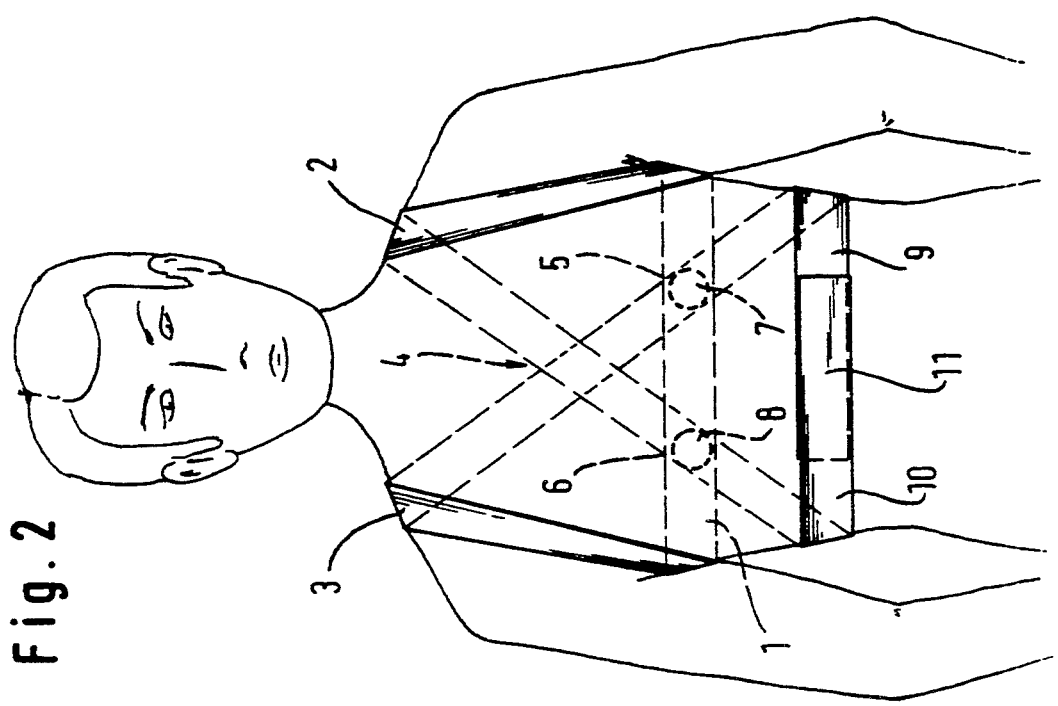
FIG. 2 shows a view of the front of the same patient with the same bandage.
Figure 1:
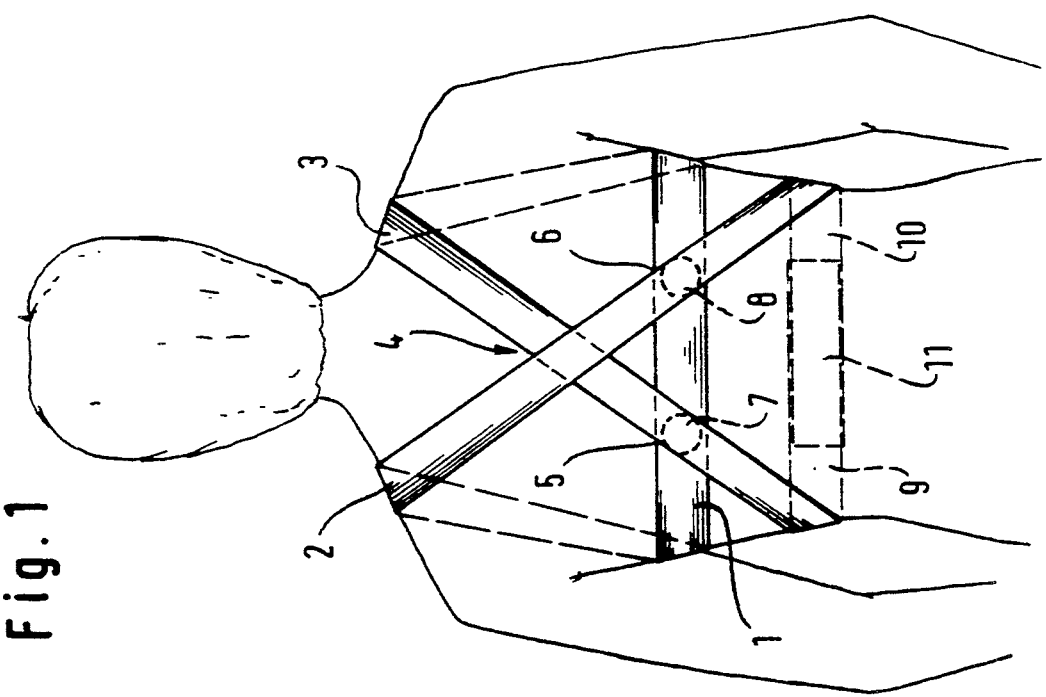
FIG. 1 shows the view of the back of a patient with the applied bandage.

The one-part bandage shown in FIGS. 1 and 2 consists of the back strap portions 1 crossing over the back, from which the two shoulder strap portions 2 and 3 are guided up to the shoulders from under the armpits of the patient, as is shown, and over the breast. Shoulder strap portions 2 and 3 then cross over the shoulders in the region of the clavicle in the direction to the back and run over the crossing place 4 lying on the back and up to back strap 1, which they cross over at support places 5 and 6. Adhesive parts, that is the hooks, 7 and 8 indicated as dotted circles are disposed at support places 5 and 6 onto back strap portion 1 on the outside and the insides of shoulder straps 2 and 3 are pressed onto them. The insides of shoulder strap portions 2 and 3 each form a coating part that is the loop portion of the Velcro fastener so that they adhere to adhesive part 7 or 8. Thus a solid but detachable joining is produced between back strap portion 1 and the two shoulder strap portions 2 and 3. In the further course of shoulder strap portions 2 and 3 from support places 5 and 6 they reach the hips of the patient and cross over the abdomen of the patient as end parts 9 and 10 until they come together in the center of the abdomen at adhesive seal 11. Adhesive seal 11 is formed on one side by the coating side of one of the end parts on the inside and on the other side by an adhesive part on the outside of the other end part (see in particular, FIG. 2). The crossing place 4 lies above back strap portion 1 at a place where it does not overlap back strap portion 1. This results from the distance shown between support places 5 and 6 or adhesive parts 7 and 8, whereby an oblique crossover of the back of the patient is produced, such that shoulder strap portions 2 and 3 cling at a relatively high position in the region of the hips and then come together over the abdomen of the patient in adhesive seal 11.

In applying the bandage, first back strap portion 1 is applied over the back of the patient, whereupon the two shoulder strap portions 2 and 3 are thrown from the breast side over the shoulders. Then shoulder strap portions 2 and 3 hanging over the back of the patient are grasped with the hands and made to cross the back and are guided to the hips and are then brought to join together at the adhesive seal over the abdomen like a girdle. The necessary tension of the bandage is thus brought about by the fact that, on the one hand, shoulder strap portion 2 and 3 are applied by pulling on end parts 9 and 10 tightly over back strap portion 1, whereby by pressing shoulder strap portions 2 and 3 against adhesive parts 7 and 8, the reciprocal attachment of back strap portion 1 and the two shoulder strap portions 2 and 3 is produced. Then, while pulling on the two end parts 9 and 10, the tension is maintained in shoulder straps 2 and 3 until end parts 9 and 10 are joined together by sealing adhesive seal 11.

Since the bandage which is shown consists of a nonelastic material, the tension adjusted upon applying the bandage remains constantly uniform, whereupon the therapeutically desired effect is created and maintained on the respective clavicle by shoulder strap 2 and/or 3.

The side of the bandage turned toward the body, at least of shoulder straps 2 and 3 and end parts 9 and 10, is formed as a coating part of an adhesive seal, so that any length of shoulder straps 2 and 3 can be adjusted by pressing on adhesive parts 7 and 8 with respect to support places 5 and 6 on back strap 1. The concerned coating parts thus completely cover the adhesive parts that lie opposite, including adhesive seal 11, so that the adhesive parts cannot damage a piece of clothing worn over the bandage.

It is apparent that modifications and changes can be made within the spirit and scope of the present invention. It is our intention, however, only to be limited by the scope of the appended claims.

As our invention we claim:

1. A one-part bandage for the clavicle, said bandage comprising:
   a back strap portion (1) adapted to extend crosswise over the back;
   shoulder strap portions (2, 3) connected to said back strap portion, said shoulder strap portions adapted to run under the armpits and extend over the clavicle, said shoulder strap portions crossing in the region of the middle of the back strap portion (1) at a crossing place (4);
   connecting end part portions (9, 10) adapted to run over the hips up to the abdomen and connect to each other;
   an adhesive seal formed of a hook and loop fastener (11) joining said end part portions together;
   said bandage being characterized by being constructed of a nonelastic material;
   said shoulder strap portions (2, 3) being applied onto said back strap portion (1) at two support places that are distant from one another on said back strap portion;
   said support places (5, 6) each formed by an adhesive seal, said adhesive seal including hooks (7, 8) disposed on the back strap portion (1) and having loops disposed on said shoulder strap portions (2, 3), said loops of said shoulder strap portions completely covering the respective hooks of the back strap portion (7, 8) when said bandage is disposed around the body.

2. The bandage according to claim 1 further characterized in that bandage is formed throughout as loops, said loops also covering the hooks of the adhesive seal (11).

3. The bandage according to claim 2 further characterized in that the adhesive seals (7, 8) on the back strap portion (1) are disposed at a distance apart such that the crossing place (4) of the shoulder strap portions (2, 3) lies above the back strap (1) and does not overlap the latter.

4. The bandage according to claim 1 further characterized in that the hooks (7, 8) on the back strap portion (1) are disposed at a distance apart such that the crossing place (4) of the shoulder strap portions (2, 3 ) lies above the back strap portion (1) and does not overlap the latter.

* * * * *